(12) United States Patent
Nagai et al.

(10) Patent No.: US 9,541,564 B2
(45) Date of Patent: *Jan. 10, 2017

(54) REAGENT FOR ASSAYING D-DIMER AND KIT OF REAGENT FOR ASSAYING D-DIMER

(71) Applicant: SYSMEX CORPORATION, Kobe-shi, Hyogo (JP)

(72) Inventors: Keisuke Nagai, Kobe (JP); Kazuaki Yamashita, Kobe (JP); Susumu Hoshiko, Kobe (JP); Takeshi Suzuki, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/131,375

(22) Filed: Apr. 18, 2016

(65) Prior Publication Data

US 2016/0231339 A1    Aug. 11, 2016

Related U.S. Application Data

(63) Continuation of application No. 13/190,146, filed on Jul. 25, 2011, now Pat. No. 9,347,957.

(30) Foreign Application Priority Data

Jul. 27, 2010    (JP) ................. 2010-168521

(51) Int. Cl.
*G01N 33/53* (2006.01)
*G01N 33/86* (2006.01)
(52) U.S. Cl.
CPC ........... *G01N 33/86* (2013.01); *G01N 2333/75* (2013.01)
(58) Field of Classification Search
CPC .... G01N 33/86; G01N 2333/75; G01N 33/50; G01N 33/53; G01N 33/566
See application file for complete search history.

(56) References Cited

U.S. PATENT DOCUMENTS

| | | |
|---|---|---|
| 5,099,004 A | 3/1992 | Nieuwenhuizen |
| 2002/0106708 A1 | 8/2002 | Thomas et al. |
| 2004/0029286 A1 | 2/2004 | Korte |
| 2006/0194272 A1 | 8/2006 | Okuda et al. |
| 2009/0305301 A1 | 12/2009 | Mirshahi et al. |

FOREIGN PATENT DOCUMENTS

| | | |
|---|---|---|
| JP | 0746104 | 4/1988 |
| JP | 2000041673 | 2/2000 |
| JP | 2000193663 | 7/2000 |
| JP | 2001354700 | 12/2001 |
| JP | 2006105633 | 4/2006 |
| JP | 2006234675 | 9/2006 |
| JP | 2006234676 | 9/2006 |
| JP | 3857468 | 12/2006 |
| WO | 0239114 | 5/2002 |
| WO | 2006118195 | 11/2006 |

OTHER PUBLICATIONS

Dempfle, "Validation, Calibration, and Specificity of Quantitative D-Dimer Assays," Seminars in Vascular Medicine, 5(4):315-320 (2005).
Extended European Search Report dated Jan. 23, 2012, issued in European Patent Application No. 11175510.4.
Hamano et al., "A novel monoclonal antibody to fibring monomer and soluble fibrin for the detection of soluble fibrin in plasma," Clinica Chimica, Acia, p. 318 (2002).
Rylatt et al., "An Immunoassay for Human D Dimer Using Monoclonal Antibodies," Thrombosis Research, 31(6):767-778 (1983).
Sukhu et al., "Comparison of an immuno-turbidometric method (sTalia d-DI) with an established enzyme linked fluorescent assay (VIDAS) d-dimer for the exclusion of venous thromboembolism," International Journal Lab. Hem., 30:200-204 (2008).

*Primary Examiner* — Gary W Counts
(74) *Attorney, Agent, or Firm* — Sughrue Mion, PLLC

(57) ABSTRACT

The present invention provides a reagent for assaying D-dimer which includes carriers sensitized to first and second monoclonal antibodies which react with D-dimer, but have different reactivity to D-dimer in which the first monoclonal antibody reacts with high- and low-molecular fractions of D-dimer, the second monoclonal antibody reacts with the high-molecular fraction, but reactivity of the second monoclonal antibody with the low-molecular fraction is different from that of the first monoclonal antibody and a kit of reagent for assaying D-dimer.

20 Claims, 3 Drawing Sheets

REAGENT FOR ASSAYING D-DIMER AND KIT OF REAGENT FOR ASSAYING D-DIMER

CROSS-REFERENCE TO RELATED APPLICATIONS

This application is a Continuation of U.S. Application Ser. No. 13/190,146, filed Jul. 25, 2011 (now U.S. Pat. 9,347,957); which claims priority based on Japanese Patent Application No. 2010-168521 filed Jul. 27, 2010.

FIELD OF THE INVENTION

The present invention relates to a reagent for assaying D-dimer to be used for measuring D-dimer which is a fibrin degradation product and a kit of reagent for assaying D-dimer.

BACKGROUND

It is known that in the field of clinical laboratory testing, in particular, blood coagulation fibrinolytic testing, D-dimer is measured. D-dimer is one type of blood coagulation molecular marker, and it is important to measure this when diagnosing various types of thrombosis which enhance the coagulation/fibrinolytic system, and DIC (disseminated intravascular coagulation syndrome), and when gaining a barometer for determining the pathosis of these and judging the effects of curing.

There are various known methods of measuring D-dimer and reagents for assaying D-dimer are also marketed. The reagents for assaying D-dimer in which one type of monoclonal antibody is sensitized to carrier particles are described in Japanese Patent Application Publication (JP-B) No. 7-46104, Japanese Patent Application Laid-Open (JP-A) No. 2000-193663, JP-A No. 2006-105633, JP-A No. 2006-234676, and Japanese Patent No. 3857468.

In diagnosis by exclusion of deep venous thrombosis, it is known that measurement of the concentration of D-dimer is useful (US2004029286 and US2009305301). In the case where a cutoff value is set for the concentration of D-dimer and the concentration of D-dimer of a subject is below the cutoff value, the subject can be determined not to have deep venous thrombosis. Therefore, there is a need for high measurement sensitivity of D-dimer in a low-density region in order to determine whether the subject has deep venous thrombosis.

In the past, the concentration of an antibody to D-dimer in an assay reagent has been improved or a sensitizer has been added into the reagent in order to improve measurement sensitivity of D-dimer. However, these methods have caused problems that background increases and a reaction solution is thickened and foamed.

SUMMARY OF THE INVENTION

The scope of the present invention is defined solely by the appended claims, and is not affected to any degree by the statements within this summary.

An object of the present invention is to provide a reagent capable of assaying D-dimer in a low-density region with high sensitivity without increasing the concentration of an antibody to D-dimer in an assay reagent or adding a sensitizer into the reagent and a reagent kit.

The present inventors have been dedicated to the study and found that when a reagent containing carriers sensitized to first and second monoclonal antibodies which react with D-dimer, but have different reactivity to D-dimer is used, the detectability of D-dimer is improved as compared with that of a conventional reagent sensitized to one type of antibody and thus D-dimer even in a low-density region can be measured, and completed the present invention.

A first aspect of the present invention is a reagent for assaying D-dimer, comprising: carriers sensitized to first and second monoclonal antibodies which react with D-dimer, but have different reactivity to D-dimer; wherein the first monoclonal antibody reacts with high-and low-molecular fractions of D-dimer, the second monoclonal antibody reacts with the high-molecular fraction, but reactivity of the second monoclonal antibody with the low-molecular fraction is different from that of the first monoclonal antibody.

A second aspect of the present invention is a reagent for assaying D-dimer, comprising: carriers sensitized to first and second monoclonal antibodies which react with D-dimer, but have different reactivity to D-dimer; wherein the first monoclonal antibody reacts with X-fraction, Y-fraction, and D-dimer, but does not react with D-and E-fractions, the second monoclonal antibody reacts with D-dimer, but does not react with X-, Y-, and E-fractions.

A third aspect of the present invention is a kit of reagent for assaying D-dimer, comprising: a first reagent containing a buffer; and a second reagent containing carrier particles sensitized to the first and second monoclonal antibodies which react with D-dimer, but have different reactivity to D-dimer; wherein the first monoclonal antibody reacts with high- and low-molecular fractions of D-dimer, the second monoclonal antibody reacts with the high-molecular fraction, but reactivity of the second monoclonal antibody with the low-molecular fraction is different from that of the first monoclonal antibody.

A fourth aspect of the present invention is a kit of reagent for assaying D-dimer, comprising: a first reagent containing a buffer; and a second reagent containing carrier particles sensitized to the first and second monoclonal antibodies which react with D-dimer, but have different reactivity to D-dimer; wherein the first monoclonal antibody reacts with X-fraction, Y-fraction, and D-dimer, but does not react with D-and E-fractions and the second monoclonal antibody reacts with D-dimer, but does not react with X-, Y-, and E-fractions.

According to the reagent and the reagent kit of the present invention, it is possible to measure D-dimer in a sample even in a low-density region which has been difficult to measure with a conventional reagent for assaying D-dimer with high sensitivity.

DETAILED DESCRIPTION OF THE PREFERRED EMBODIMENTS

Figure 1:
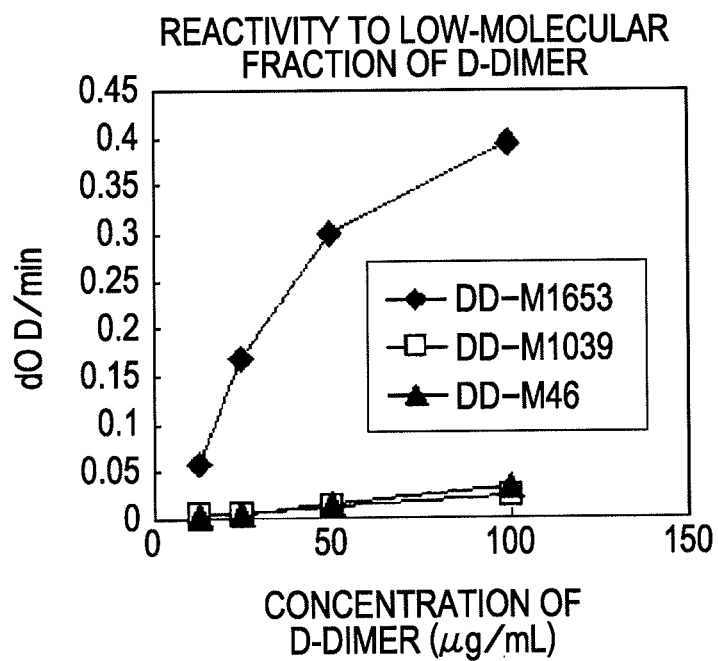
FIG. 1 is a graph showing differences in reactivity among DD-M1653 antibody, DD-M1039 antibody, and DD-M46 antibody to the fibrin/fibrinogen degradation products.
Figure 1:
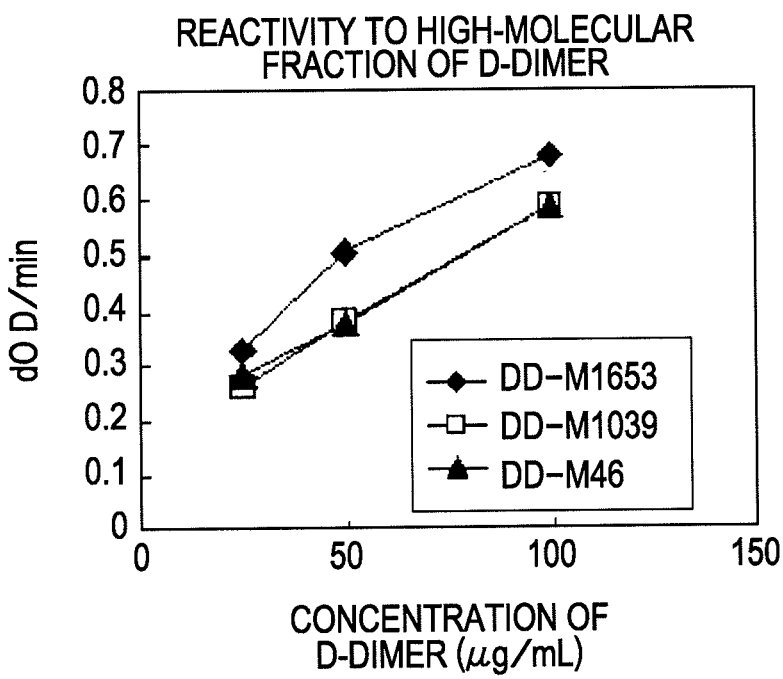

The preferred embodiments of the present invention will be described hereinafter with reference to the drawings.

The present invention is a reagent for assaying D-dimer containing carriers sensitized to first and second monoclonal antibodies which react with D-dimer, but have different reactivity to D-dimer (hereinafter also referred to as a reagent of the present invention).

The term "D-dimer" is a fibrin degradation product that is obtained when a stabilized fibrin which is a polymer that is formed when fibrinogen in blood coagulates due to effects of an enzyme such as thrombin is degraded by an enzyme such as plasmin.

D-dimer is also known as a generic name for DD/E fractions or multimers of the DD/E fractions in the art. Known examples of the multimers of the DD/E fractions include DXD/YY fractions (trimers of DD/E fractions), YXY/DXXD fractions (pentamers of DD/E fractions), and DXXD/YXXY fractions (heptamers of DD/E fractions). In the art, D-dimer and the multimers of the DD/E fractions are collectively referred to as "XDP fraction".

In the art, it is known that an enzyme, such as plasmin degrades fibrinogen present in the blood. When fibrinogen is degraded by an enzyme (e.g. plasmin), fibrinogen degradation products such as D-, E-, X-, and Y-fractions (i.e., constituent elements of the DD/E fractions) are produced. Thus, D-dimer produced by degradation of the stabilized fibrin and a fibrinogen degradation product produced by degradation of fibrinogen are mixed in the blood of a patient with thrombosis.

The term "high-molecular fraction of D-dimer" herein means a fibrin degradation product obtained by degrading the stabilized fibrin by an enzyme, such as plasmin for a short time. Examples of the high-molecular fraction of D-dimer include fibrin degradation products obtained by degrading the stabilized fibrin by plasmin for 0.25 hour to 4 hours, preferably for 0.25 hour to 2 hours.

The term "low-molecular fraction of D-dimer" herein means a fibrin degradation product obtained by degrading the stabilized fibrin by an enzyme, such as plasmin for a long time. Examples of the low-molecular fraction of D-dimer include fibrin degradation products obtained by degrading the stabilized fibrin by plasmin for 10 to 30 hours, preferably for 15 to 25 hours.

The antibody to be used for the reagent of the present invention is not particularly limited as long as it is two types of monoclonal antibodies which react with D-dimer, but have different reactivity to D-dimer. Hereinafter, one of the two types of monoclonal antibodies is referred to as a "first monoclonal antibody" and the other is referred to as a "second monoclonal antibody". Preferable examples of such antibodies include a first monoclonal antibody which reacts with high-and low-molecular fractions of D-dimer and a second monoclonal antibody which reacts with the high-molecular fraction, but has reactivity with the low-molecular fraction which is different from that of the first monoclonal antibody.

The first monoclonal antibody to be used for the reagent of the present invention is more preferably an antibody which reacts with X-fraction, Y-fraction, and D-dimer, but does not react with D-fraction and E-fraction.

The second monoclonal antibody to be used for the reagent of the present invention is more preferably an antibody which reacts with D-dimer, but does not react with X-fraction, Y-fraction, and E-fraction. The second monoclonal antibody may be an antibody which reacts with D-fraction or an antibody which does not react with D-fraction.

The first and second monoclonal antibodies may be derived from any mammals, such as mice, rats, hamsters, rabbits, goats, and horses. Among them, mice are preferred.

The isotype of the antibodies may be any of IgG, IgM, IgE, and IgA. The antibodies contain antibody fragments and the derivatives thereof. Specific examples thereof include Fab fragments and F(ab')2 fragments.

The first and second monoclonal antibodies can be obtained by any known immunological procedure in the art. That is, a hybridoma which produces a monoclonal antibody can be obtained by arbitrarily mixing D-dimer as an antigen with an adjuvant, immunizing an animal with the mixture, and allowing B-lymphocytes derived from the animal to fuse with various kinds of myeloma cells.

Specifically, the first and second monoclonal antibodies which are used for the reagent of the present invention can be obtained in the following manner.

(Obtainment of Antigen)

D-dimer to be used as an antigen can be obtained by reacting an enzyme capable of degrading fibrin like plasmin with fibrin. Preferably, the D-dimer contains a fraction having a molecular weight higher than that of DD/E fractions. Examples thereof include dimers to pentamers of DD/E fractions. Recombinant D-dimer obtained by any known genetic engineering procedure in the art based on an amino acid sequence of D-dimer may be used as an antigen.

As for the fibrin that is used as the material of D-dimer, commercially available fibrin may be used or fibrin may be prepared by reacting fibrinogen with thrombin, factor XIII, and calcium salt.

(Immunization Method)

It is possible to immunize an animal with an antigen solution obtained by arbitrarily mixing the antigen obtained in the above manner with an adjuvant and dissolving or suspending in a suitable buffer. The concentration of the antigen in the antigen solution is preferably about from 50 to 500 µg/ml. When the immunogenicity of the antigen is low, the antigen may be arbitrarily bound to carrier proteins such as albumin and keyhole limpet hemocyanin.

As for the adjuvant, any known adjuvant in the art may be used. Examples of the adjuvant include Freund's complete adjuvant (FCA), Freund's incomplete adjuvant (FIA), Ribi (MPL), Ribi (TDM), Ribi (MPL and TDM), Pertussis vaccine (*Bordetella pertussis* vaccine), Muramyldipeptide (MPD), Aluminum adjuvant (ALUM), and combinations thereof. A particularly preferable combination is that FCA is used in the primary immunization and the FIA and the Ribi adjuvant are used in booster.

The animal to be immunized may be any of mice, rats, hamsters, horses, goats, and rabbits. Mice are preferred and a BALB/c mouse is more preferred.

The immunization method can be suitably selected depending on the type of antigen to be used and the presence or absence of the adjuvant. For example, when a mouse is used, 0.05 to 1 ml of (antigen: 10 to 200 µg) an adjuvant-antigen mixture solution is injected to the abdominal cavity, under the skin, muscle, or tail vein. The booster is performed once to four times about every 4 to 21 days after the primary immunization. After 1 to 4 weeks, the final immunization is performed. Immunisation may be performed without using the adjuvant for the antigen solution by increasing the amount of antigen for intraperitoneal injection. Blood is collected and the antibody titer is measured about 5 to 10 days following booster. The antibody titer can be measured in accordance with any known method in the art, such as the antibody titer assay to be described later. About 3 to 5 days after the final immunization, the spleen is extracted from the immunized animal and spleen cells are separated to obtain antibody-producing cells.

(Preparation of Monoclonal Antibody)

A monoclonal antibody can be prepared in accordance with any known method in the art, such as a method described in Kohler and Milstein, Nature, 256, 495-497 (1975).

The myeloma cells to be used may be derived from any of mice, rats, and humans. Examples thereof include established myeloma cells such as mouse myeloma P3X63-Ag8, P3X63-Ag8-U1, P3NS1-Ag4, SP2/o-Ag14, and P3X63-Ag8/653. Some myeloma cells produce an immunoglobulin light chain, and when such a myeloma cell is used as a subject of fusion, this light chain may be randomly bound to an immunoglobulin heavy chain produced by the antibody-producing cell. Accordingly, it is preferable to use, particularly a myeloma cell not producing an immunoglobulin light chain, for example, P3X63-Ag8/653 or SP2/o-Ag14. The antibody-producing cells and myeloma cells are preferably derived from the same animals, particularly inbred animals.

The method of producing a hybridoma by fusing the antibody-producing cell with the myeloma cell is not particularly limited. Examples thereof include a method of using polyethylene glycol (PEG), a method of using Sendai virus, and a method of using an electric fusion apparatus. In the PEG method, spleen cells and myeloma cells may be suspended in a mixing ratio of 1:1 to 10:1, preferably 5:1 to 10:1 in a suitable medium or buffer containing about 30 to 60% PEG (average molecular weight: 1000 to 6000) and then incubated for about 30 seconds to 3 minutes under the conditions of a temperature of about 25 to 37° C. and pH 6 to 8. After the incubation is finished, the cells are washed to remove the PEG solution, suspended again in the medium, then seeded in a microtiter plate and continued to be cultured.

A hybridoma can be selected by culturing the cells fused in the above manner on a selective medium. The selective medium may be a culture medium in which only the fused cells may increase. For example, a hypoxanthine-aminopterin-thymidine (HAT) culture medium is used. Selection of the hybridoma is initiated by exchanging a part of the medium, preferably about half of the medium, with the selective medium, usually 1 to 7 days after the fusion procedure, culturing while exchanging the medium every 2 to 3 days in the same manner as described above, then selecting wells where colonies of hybridoma grow by microscopic observations.

The presence of the desired antibody in the thus obtained hybridoma can be confirmed by collecting a culture supernatant of the hybridoma and performing antibody titer assay. The antibody titer assay can be performed by any known method in the art. For example, the antibody can be detected by a process of adding a culture supernatant serially diluted to an antigen protein immobilized on a solid phase and reacting the resultant product with a second antibody (e.g. antiglobulin antibody, anti-IgG antibody, and anti-IgM antibody) labeled with a fluorescent substance, an enzyme or a radioisotope (RI).

The hybridoma in which production of a desired antibody has been confirmed by the antibody titer assay can be separated into monoclones by limiting dilution, soft agar assay, fluorescence excitation cell sorter assay, or the like. For example, in the case of the limiting dilution, the hybridoma which produces a target antibody can be isolated by culturing a hybridoma colony by serial dilution in a culture medium at a concentration of 1 cell/well.

A method of obtaining a monoclonal antibody from a hybridoma can be suitably selected according to the requirement of a monoclonal antibody and characteristics of a hybridoma. Examples thereof include a method of obtaining a monoclonal antibody from the ascitic fluid of a mouse to which the hybridoma has been transplanted and a method of obtaining a monoclonal antibody from a culture supernatant prepared by culturing cells. In the case where a hybridoma that can proliferate in the mouse intraperitoneal cavity is used, a high concentration (several mg/mL) of monoclonal antibody can be obtained from the peritoneal fluid. In the case of a hybridoma that cannot proliferate in vivo, a monoclonal antibody can be obtained from the culture supernatant of a cell culture. In this case, although the monoclonal antibody is obtained at a lower yield, the antibody is less contaminated with immunoglobulin and impurities, and the antibody can be easily purified.

In the case where an antibody is obtained from the mouse peritoneal cavity to which a hybridoma has been transplanted, peritoneal fluid stored is collected about 1 week to 3 weeks after hybridomas (about 106 cells or more) has been transplanted into the peritoneal cavity of BALB/c mouse with an immunosuppressive agent such as pristane (2,6,10, 14-tetramethylpentadecane) previously administered. In the case of heterologous hybridoma implantation, a nude mouse and an irradiated mouse are preferably used.

On the other hand, in the case where an antibody is collected from a cell culture supernatant, the hybridoma is cultured by a culture method such as the high-density culture method and the spinner flask culture method, in addition to the stationary culture method that is used for maintaining cells, and a culture supernatant containing an antibody is obtained. Addition of serum to a culture medium causes the medium to contain impurities such as other antibodies and albumin, resulting in a frequently complicated purification procedure of antibody. Therefore, it is desirable to reduce the amount of serum for adding to the culture medium. It is more preferable to naturalize a hybridoma to a serum-free medium according to the usual method and culture with the serum-free medium. This process allows for easy purification of antibody.

A monoclonal antibody can be purified from peritoneal fluid or culture supernatant by known methods such as the fractionation by salting-out with ammonium sulfate or sodium sulfate, polyethylene glycol fractionation, ethanol fractionation, DEAE ion-exchange chromatography, and gel-filtration chromatography.

When a target monoclonal antibody is a mouse IgG, the antibody can be purified by affinity chromatography using a protein A-bound carrier or an anti-mouse immunoglobulin-bound carrier.

Examples of the first monoclonal antibody to be used for the reagent of the present invention include a mouse antibody produced by a hybridoma deposited with the National Institute of Advanced Industrial Science and Technology under Accession No. FERM BP-11393 on Feb. 17, 2004 (hereinafter also referred to as "DD-M1653 antibody").

Examples of the second monoclonal antibody to be used for the reagent of the present invention include mouse antibodies produced by hybridomas deposited with the National Institute of Technology and Evaluation, 2-5-8 Kazusakamatari Kisarezu-shi, Chiba-ken 292-0818, Japan, under the terms of the Budapest Treaty on the International Recognition of the Deposit of Microorganisms for the Purposes of Patent Procedure under Accession Nos. NITE BP-968 and NITE BP-969 on Jul. 23, 2010 (hereinafter referred to as "DD-M1039 antibody" and "DD-M46 antibody", respectively).

The ratio of concentration of the first and second monoclonal antibodies in the reagent for assaying D-dimer of the present invention is not particularly limited, for example, it can be suitably selected from the range of 9:1 to 1:9.

The reagent for assaying D-dimer of the present invention includes a carrier sensitized to first and second monoclonal antibodies which react with D-dimer, but have different reactivity to D-dimer. Examples of the carrier include an organic polymer compound, an inorganic compound, and red blood cells. Examples of the organic polymer compound include insoluble agarose, insoluble dextran, cellulose, latex, polystyrene, a styrene-methacrylic acid copolymer, a styrene-glycidyl(meth)acrylate copolymer, a styrene-styrene sulfonate copolymer, a methacrylic acid polymer, an acrylic acid polymer, an acrylonitrile-butadiene-styrene copolymer, a vinyl chloride-acrylic ester copolymer, and polyvinyl acetate acrylate. Examples of the inorganic compound include silica and alumina.

The shape of the carrier is not particularly limited and it may be any shape, such as a spherical shape and a plane shape. In the case of the spherical shape, the average diameter of particles can be suitably selected by a measuring machine and a suitable range is usually from 0.05 to 0.5 µm. As a particle material, latex is particularly preferred.

As a method of sensitizing the first and second monoclonal antibodies to carriers, either a physical adsorption method or a chemical conjugation method, known in the art, may be used. Since support operation is simple, the physical adsorption method is preferred.

When the carriers are particles, the carrier particles may be carrier particles sensitized to both first and second monoclonal antibodies or may be a mixture of carrier particles sensitized to the first monoclonal antibody and carrier particles sensitized to the second monoclonal antibody. When sensitization conditions of the first and second monoclonal antibodies to the carrier particles are different, it is preferable to individually sensitize the antibodies to the carrier particles.

When the carrier particles are latex particles, it is preferable that the carrier particles sensitized to the first and second monoclonal antibodies are suspended in a suitable buffer. In that case, the concentration of the latex particles in the suspension is preferably from 0.5 to 10 mg/ml, more preferably from 0.75 to 1.85 mg/ml. The concentration of the monoclonal antibodies in the suspension is preferably from 0.1 to 10 mg/ml, more preferably from 0.5 to 2 mg/ml.

It is preferable for the buffer solution to have a buffering effect in the range of pH 5 to 10, preferably pH 6 to 9. Specific examples thereof include a phosphate buffer solution, an imidazole buffer solution, triethanolamine hydrochloric acid, and a Good buffer solution. Examples of the Good buffer solution include buffer solutions such as MES, Bis-Tris, ADA, PIPES, Bis-Tris-Propane, ACES, MOPS, MOPSO, BES, TES, HEPES, HEPPS, Tricine, Tris, Bicine, and TAPS. Among them, MOPSO is preferred.

The above buffer may contain additives such as a protein stabilizing agent (e.g. BSA), an antiseptic (e.g. sodium azide and phenylmethanesulfonyl fluoride), a pH adjustor, a sensitizer (e.g. polyvinylpyrrolidone, polyanion, polyethylene glycol, and polysaccharide), mineral salt (e.g. sodium chloride and calcium chloride), and a background inhibitor (e.g. human anti-mouse antibody (HAMA) absorbent).

As an embodiment of the reagent of the present invention, a kit of reagent for assaying D-dimer can be listed (hereinafter also referred to as a reagent kit of the present invention). The reagent kit of the present invention includes a first reagent containing a buffer and a second reagent containing carrier particles sensitized to the first and second monoclonal antibodies which react with D-dimer, but have different reactivity to D-dimer.

The reagent kit of the present invention is a reagent kit for detecting D-dimer in a sample by immunoassay, assay for reacting, for example, latex particles sensitized to the first and second monoclonal antibodies with D-dimer in the biological sample (latex agglutination), or the like.

The form of the reagent kit of the present invention is a two reagent-type kit composed of the first and second reagents as described above, however, it may be a one reagent-type kit composed of a reagent. From the viewpoint of measurement accuracy, the form of the reagent kit is preferably a two reagent-type kit composed of the first and second reagents. In a more preferable embodiment, the reagent kit of the present invention includes the first reagent containing a buffer and the second reagent composed of the reagent for assaying D-dimer of the present invention.

A buffer contained in the first reagent configuring the reagent kit of the present invention includes a buffer similar to a buffer which may be used for suspending carrier particles in the reagent of the present invention. The first reagent may contain additives such as the protein stabilizer, an antiseptic, a pH adjustor, a radiosensitizing agent, and mineral salt as described above.

The above first reagent may contain an antibody which reacts with D-dimer. Examples of the antibody include the first monoclonal antibody and/or the second monoclonal antibody contained in the above reagent of the present invention. The antibody contained in the first reagent is preferably the first monoclonal antibody, more preferably DD-M1653 antibody. The concentration of the monoclonal antibody in the first reagent is preferably from 1 to 100 µg/ml, more preferably from 5 to 50 µg/ml.

An antibody having reactivity to D-dimer as well as reactivity to the fraction having a structure similar to D-dimer, such as X-fraction and/or Y fraction is included in the monoclonal antibody contained in the first reagent. Even if X- and Y-fractions, i.e., components having a structure similar to D-dimer are present in a specimen, the monoclonal antibody in the first reagent is bound to those fractions by adding the monoclonal antibody having such reactivity to the first reagent. Therefore, it is considered that the reactivity between the monoclonal antibody sensitized to carriers in the second reagent to be subsequently added and these fractions is suppressed. This is considered because X- and Y-fractions have only one reactive site to the monoclonal antibody, while D-dimer has a plurality of reactive sites to the monoclonal antibody. Consequently, the D-dimer to be measured can react with high specificity to the monoclonal antibody sensitized to the carriers, thereby allowing for more accurate measurement of the concentration of D-dimer.

Hereinafter, a method of assaying D-dimer in a biological sample using a kit of reagent for assaying D-dimer of the present invention will be specifically described.

First, the first reagent containing a buffer is mixed with a biological sample, which is incubated. Here, examples of the biological sample include serum, plasma, and urine. The capacity ratio when mixing the first reagent with the biological sample may be from about 5:1 to 50:1. The incubation time may be from about 1 minute to 10 minutes.

Subsequently, the second reagent containing carrier particles sensitized to the first and second monoclonal antibodies which have different reactivity to D-dimer is added to a mixture of the first reagent and the biological sample. The capacity ratio when mixing the mixture with the second reagent may be from about 1:0.05 to 1:1.5.

When the second reagent is added and mixed, aggregation of carrier particles in the second reagent and D-dimer is caused by an antigen-antibody reaction. The aggregation level is measured as the absorbance variation per minute. The measurement is preferably performed with an optical apparatus capable of measuring intensity of scattered light, absorbance or intensity of transmitted light. The measurement wavelength can be suitably selected from the range of 300 to 2400 nm, preferably the range of 400 to 1200 nm, more preferably the range of 600 to 1000 nm.

The concentration and/or amount of D-dimer in the biological sample can be calculated from the measured absorbance variation using a calibration curve obtained by measuring a concentration-known D-dimer reference material.

The reagent kit of the present invention can be utilized for a method of mixing the first reagent with the second reagent, adding a biological sample to a mixture of both reagents, and optically measuring the aggregation level of carrier particles.

EXAMPLES

In the following examples, the present invention will be described in detail. However, the present invention is not intended to be limited to the following embodiments.

1. Confirmation of Reactivity of Antibodies by Immunoprecipitation Method

Differences in reactivity among antibodies to the fibrin/fibrinogen degradation products were examined by the following immunoprecipitation method using DD-M1653 antibody as the first monoclonal antibody and DD-M1039 and DD-M46 antibodies as the second monoclonal antibody.

A fibrin degradation product (D-dimer) and fibrinogen degradation products (X-, Y-, D-, and E-fractions) were reacted with antibodies, and then an antigen-antibody reaction product was adsorbed to goat anti-mouse Ig antibody-sepharose 4B. The sepharose 4B having the adsorbed antigen-antibody reaction product was washed with a cleaning liquid (10 mM NaPB (pH 7.0)), followed by release of the conjugated antigens in a diluent for sample for SDS electrophoresis (10% glycerol, 2% SDS, 0.01% BPB containing 62.5 mM Tris-HCl (pH6.8)). The released antigens were subjected to SDS polyacrylamide gel electrophoresis and immersed in a transcription buffer (25 mM tris, 192 mM glycine, 0.02% SDS, 20% methanol (pH 8.3)) at 100 V for 1 hour so as to be transferred to a PVDF membrane (Bio-rad). The transferred PVDF membrane was blocked with a blocking buffer (5% skim milk containing 10 mM NaPB (pH 7.0)). Then, the PVDF membrane was immersed in a rabbit anti-fibrinogen polyclonal antibody solution diluted to 0.1 mg/ml with the 5% skim milk containing 10 mM NaPB (pH 7.0), followed by incubation at room temperature for 3 hours. The PVDF membrane was washed with a cleaning liquid. Then, the PVDF membrane was immersed in goat-anti-rabbit Ig antibody labeled POD (DAKO) which had been 500-fold diluted with a 2% skim milk containing 10 mM NaPB (pH 7.0), followed by reaction at room temperature for 1 hour. The PVDF membrane was washed with a cleaning liquid and developed using 4-chloro-1-naphthol/$H_2O_2$ (Bio-rad) to detect the antigens. The results were shown in Table 1.

TABLE 1

|            | DD-M1653 | DD-M1039 | DD-M46 |
|------------|----------|----------|--------|
| X-fraction | +        | −        | −      |
| Y-fraction | +        | −        | −      |
| D-fraction | −        | −        | w      |
| E-fraction | −        | −        | −      |
| D-dimer    | +        | +        | +      |

In Table 1, the mark "+" indicates that each antibody reacts with each fraction, the mark "−" indicates that each antibody does not react with each fraction, and the mark "w" indicates that each antibody slightly reacts with each fraction.

From Table 1, it is found that DD-M1653 antibody reacts with X-fraction, Y-fraction, and D-dimer, but does not react with D- and E-fractions. Further, it is found that DD-M1039 antibody and DD-M46 antibody react with D-dimer, but do not react with X-, Y-, and E-fractions.

2. Preparation of Reagent for Assaying D-Dimer and Reagent Kit (1) Preparation of High- and Low-Molecular Fractions of D-Dimer Human fibrinogen (Human Fibrinogen Plasminogen Depleted; Enzyme Research Lab) was dissolved in 0.05 M TRIS Buffer (PH 7.4) at a concentration of 6.62 mg/ml, followed by addition of calcium chloride (final concentration: 25 mM), human thrombin (2 U/ml), and factor XIII (final concentration; 10 µg/ml, Fibrogammin P; Aventis Pharma Limited) to the resultant solution. The fibrinogen was converted to fibrin by incubation at 37° C. for 18 hours.

Fibrin blocks formed in each reaction solution was washed by stirring in 300 mL of 0.05M TRIS buffer for about 1 hour. The washed fibrin blocks were separated with a cutter knife, which was resuspended in 3.5 ml (for high-molecular fraction) and 1.5 ml (for low-molecular fraction) of 0.05M TRIS buffer. Plasmin was added to each of the suspensions at a final concentration of 25 mU/ml and reacted while stirring at 37° C.

0.75 hour later, aprotinin was added to the reaction solution for high-molecular fraction at a final concentration of 1000 U/ml to stop the degradation reaction. The resultant product was filtrated with a 5 µm-filter to obtain a high-molecular fraction of D-dimer (0.75-hour digest of fibrin with plasmin). 20 hours after addition of plasmin, aprotinin was added to the reaction solution for low-molecular fraction at a final concentration of 1000 U/ml to stop the degradation reaction. The resultant product was filtrated with a 5 µm-filter to obtain a low-molecular fraction of D-dimer (20-hour digest of fibrin with plasmin).

(2) Preparation of Reagent for Assaying D-Dimer (2-1) Preparation of First Reagent DD-M1653 antibody was added to a buffer prepared by mixing each reagent at final concentrations shown in Table 2 so as to be a final concentration of 10 µg/ml, which was mixed. The mixed liquid thus prepared was adjusted to pH 7.1 with 1M aqueous sodium hydroxide and diluted to 1 liter with ultrapure water, resulting in production of a first reagent containing a buffer.

TABLE 2

| Reagent | Final concentration | Manufacturer |
|---------|---------------------|--------------|
| MOPSO   | 75.5 mM             | DOJINDO LABORATORIES |

TABLE 2-continued

| Reagent | Final concentration | Manufacturer |
|---|---|---|
| Sodium chloride | 0.677M | MANAC Incorporated. |
| Sodium azide | 0.10% | Kishida Chemical Co., Ltd. |
| BSA | 1.5% | PROLIANT Inc. |
| Ultrapure water | Suitable amount | |

(2-2) Preparation of Reagent for Assaying D-Dimer Containing Carrier Particles Sensitized to Antibodies
(2-2-1) Conversion of Antibody to F(ab')2
(i) Conversion of DD-M1653 Antibody to F(ab')2

Pepsin (about 3,500 unit/mg prot.) (SIGMA) and DD-M1653 antibody were mixed in a 50 mM citrate buffer solution (pH 3.7) at a weight ratio of 1:20 and the mixture was allowed to stand at 37° C. for 1 hour. A 3M tris solution was added to the mixture to adjust the pH to 8.0 and a mixed solution was prepared.

A column filled with SUPERDEX® 200 pg (GE Healthcare) was placed in an AKTA prime plus system (GE Healthcare), and the column was equilibrated with an equilibration buffer (3.3 mM 3,3-dimethyl glutaric acid containing 3.3 mM tris(hydroxymethyl)amino methane).

While passing the equilibration buffer through a column at a flow rate of 1 ml/min, one-hundredth or less of the gel volume of the above mixed solution was applied thereto, and fractionation of the column eluent was started immediately. A volume up to about 1.5-fold of the gel volume was collected and peaks were collectively recovered based on the absorbance of the obtained solution. The absorbance of the recovered solution was measured to calculate the antibody concentration.

(ii) Conversion of DD-M1039 Antibody to F(ab')2

Papain (about 2.8 unit.) (SIGMA) and L-cysteine, at final concentrations of 2 mg/ml and 6.1 mg/ml, respectively, were dissolved in a 0.1M acetic acid buffer (pH 5.5)/3 mM EDTA (hereinafter referred to as an acetic acid buffer). The resultant mixture was incubated at 37° C. for 30 minutes. The reaction solution was converted to an acetic acid buffer using an ultrafiltration centrifuge tube (Amicon YM-5) (corresponding to a cutoff molecular weight of 10,000); Millipore). The concentration of papain was determined from the absorbance of the obtained solution. DD-M1039 antibody was dissolved in the solution so that the weight of papain was one twentieth of the antibody. Then, the resultant solution was incubated at 37° C. for 30 minutes, followed by addition of iodoacetamide to the obtained reaction solution at a final concentration of 30 mM.

A column filled with SUPERDEX® 200 pg (GE Healthcare) was placed in an AKTA prime plus system (GE Healthcare), and the column was equilibrated with an equilibration buffer (3.3 mM 3,3-dimethyl glutaric acid containing 3.3 mM tris(hydroxymethyl)amino methane).

While passing the equilibration buffer through a column at a flow rate of 1 ml/min, one-hundredth or less of the gel volume of the above mixed solution was applied thereto, and fractionation of the column eluent was started immediately. A volume up to about 1.5-fold of the gel volume was collected and peaks were collectively recovered based on the absorbance of the obtained solution. The absorbance of the recovered solution was measured to calculate the antibody concentration.

(iii) Conversion of DD-M46 Antibody to F(ab')2

Conversion of DD-M46 antibody to F(ab')2 was performed in the same manner as described in (ii) of Conversion of DD-M1039 antibody to F(ab')2 except that DD-M46 antibody was used in place of DD-M1039 antibody.

(2-2-2) Sensitization of Antibody to Latex Particles
(i) Sensitization of DD-M1653 Antibody to Latex Particles DD-M1653 antibody was mixed with a solution of 50 mM 2-hydroxy-3-morpholinopropanesulfonic acid/150 mM NaCl so that the final concentration when DD-M1653 antibody was converted to F(ab')2 was 1.25 mg/ml. Then, the mixed solution was mixed with a 25% (weight ratio) latex solution (particle diameter of 0.238 µm; SEKISUI MEDICAL CO., LTD.).

A solution of 50 mM 2-hydroxy-3-morpholinopropanesulfonic acid/150 mM NaCl solution/2% BSA was added, in an equivalent amount, to the resultant mixture, which was mixed, followed by centrifugation at 10° C. and 38400×g for 60 minutes. The supernatant was removed and a solution of 50 mM 2-hydroxy-3-morpholinopropanesulfonic acid/150 mM NaCl solution/2% BSA/3% sucrose, in an amount equal to that of the supernatant, was added to the precipitate.

The mixed liquid thus obtained was sonicated using an ultrasonic homogenizer (manufactured by Otake Seisakusho) under ice-cooling conditions. Further, the resultant product was sonicated using an ultrasonic treatment apparatus (Dr. Hielscher Gmbh UP-200S) under ice-cooling conditions to obtain a suspension of latex particles sensitized to DD-M1653 antibody.

(ii) Sensitization of DD-M1039 Antibody to Latex Particles

DD-M1039 antibody was mixed with a solution of 50 mM 2-hydroxy-3-morpholinopropanesulfonic acid/150 mM NaCl so that the final concentration when DD-M1039 antibody was converted to F(ab')2 was 1.25 mg/ml. A suspension of latex particles sensitized to DD-M1039 antibody was prepared in the same manner as described in the above (i) of Sensitization of DD-M1653 antibody to latex particles.

(iii) Sensitization of DD-M46 Antibody to Latex Particles

DD-M46 antibody was mixed with a solution of 50 mM 2-hydroxy-3-morpholinopropanesulfonic acid/150 mM NaCl so that the final concentration when DD-M46 antibody was converted to F(ab')2 was 1.56 mg/ml. A suspension of latex particles sensitized to DD-M46 antibody was prepared in the same manner as described in the above (i) of Sensitization of DD-M1653 antibody to latex particles.

(2-2-3) Preparation of Second Reagent

A reagent for assaying D-dimer containing carrier particles sensitized to two types of monoclonal antibodies was prepared by mixing a suspension of latex particles sensitized to DD-M1653 antibody with a suspension of latex particles sensitized to DD-M1039 antibody or DD-M46 antibody. The reagent for assaying D-dimer was used as the second reagent for the following measurement.

(3) Confirmation of Reactivity of Antibodies to D-Dimer by Latex Agglutination

Differences in reactivity among DD-M1653 antibody, DD-M1039 antibody, and DD-M46 antibody to the fibrin/fibrinogen degradation products were examined by the latex agglutination according to the following procedures.

The high-and low-molecular fractions of D-dimer prepared in the above (1) were 100-fold diluted with a TBST buffer to produce specimens. 6 µl of the specimens was mixed with 84 µl of the first reagent prepared in the above (2-1) and incubated at 37° C. for 3 minutes. The latex agglutination reaction was started by mixing the obtained reaction solution with 84 µl of a suspension of latex particles individually sensitized to the antibodies prepared in the above (2-2). The absorbance at a wavelength of 800 nm after 1 minute and 2 minutes from the start of the reaction was measured using CS-2000i (SYSMEX CORPORATION). The absorbance variation per minute was determined from these measurement results. The results are shown in FIG. 1.

As is apparent from FIG. 1, DD-M1653 antibody reacts with high- and low-molecular fractions of D-dimer. It is found that DD-M1039 antibody and DD-M46 antibody react with the high-molecular fraction of D-dimer, but have reactivity with the low-molecular fraction of D-dimer which is different from that of DD-M1653 antibody, and these antibodies have weak reactivity with the low-molecular fraction of D-dimer as compared with DD-M1653 antibody. That is, it is found that DD-M1653 antibody, DD-M1039 antibody, and DD-M46 antibody have different reactivity to D-dimer.

Therefore, the reagent for assaying D-dimer prepared in the above (2-2) is a reagent containing carrier particles sensitized to the first and second monoclonal antibodies which have different reactivity to D-dimer.

3. Examination of Reactivity of Reagent for Assaying D-Dimer of Present Invention to D-Dimer A D-dimer reference standard was measured using the reagent for assaying D-dimer of the present invention prepared in the above 2.

The reagent produced in the above 2. (2-1) was used to prepare the first reagent. The reagent produced in the above 2. (2-2) was used to prepare the second reagent. The mixing percentage (volume ratio) of the suspension of latex particles to which each of the antibodies are individually sensitized in the second reagent is shown in Table 3 below. The total amount of the antibodies in the second reagent is the same as those of any mixing percentage of the second reagents.

TABLE 3

| | | Comparative Example 1 | Example 1 | Example 2 | Example 3 | Comparative Example 2 |
|---|---|---|---|---|---|---|
| Mixing percentage of antibody | DD-M1653 | 100% | 90% | 75% | 50% | 0% |
| | DD-M1039 | 0% | 10% | 25% | 50% | 100% |

| | | Comparative Example 3 | Example 4 | Example 5 | Example 6 | Comparative Example 4 |
|---|---|---|---|---|---|---|
| Mixing percentage of antibody | DD-M1653 | 100% | 90% | 75% | 50% | 0% |
| | DD-M46 | 0% | 10% | 25% | 50% | 100% |

A reference standard of D-dimer NEO (SYSMEX CORPORATION) was diluted to prepare a D-dimer solution having a concentration of 1 μg/ml. The solution was used as a specimen. 6 μl of the specimen and 84 μl of the first reagent were mixed and incubated at 37° C. for 3 minutes. The latex agglutination reaction was started by mixing the obtained reaction solution with 84 μl of each of the second reagents of Examples 1 to 6 and Comparative examples 1 to 4. The absorbance at a wavelength of 800 nm after 1 minute and 2 minutes from the start of the reaction was measured using CS-2000i. The absorbance variation per minute was determined from these measurement results. The results are shown in FIGS. 2 and 3.

Figure 2:
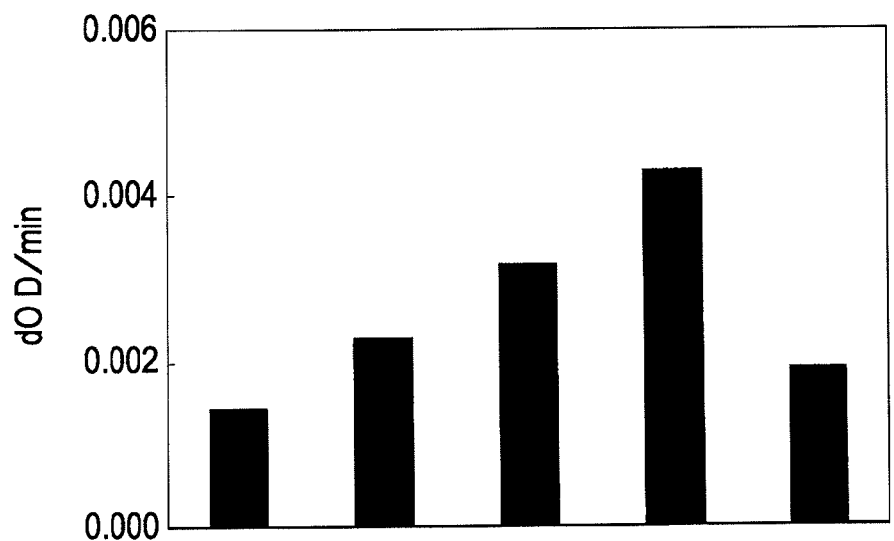
FIG. 2 is a graph showing the absorbance variation per minute at a wavelength of 800 nm when a D-dimer reference standard is measured using each of the second reagents of Examples 1 to 3 and Comparative examples 1 and 2.
Figure 3:
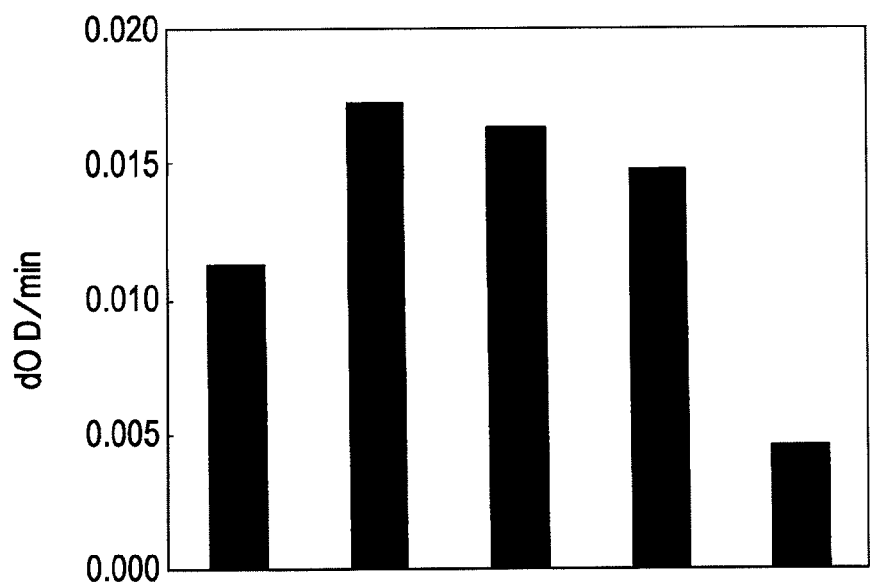
FIG. 3 is a graph showing the absorbance variation per minute at a wavelength of 800 nm when a D-dimer reference standard is measured using each of the second reagents of Examples 4 to 6 and Comparative examples 3 and 4.

As is apparent from FIGS. 2 and 3, the reagents for assaying D-dimer of Examples 1 to 6 have high reactivity to D-dimer compared with the reagents of Comparative examples.

4. Examination of Measurement Sensitivity of Reagent for Assaying D-Dimer of Present Invention to D-Dimer in Low-Density Region Concerning the measurement sensitivity to D-dimer in a low-density region, the reagent for assaying D-dimer (Example 1) of the present invention was compared with the conventional reagent for assaying D-dimer (Comparative example 1).

A reference standard of D-dimer NEO (SYSMEX CORPORATION) was diluted to prepare a D-dimer solution having a concentration of 0.25 μg/ml. The solution was used as a specimen. 6 μl of the specimen and 84 μl of the first reagent prepared in (2-1) of Experimental example 1 were mixed and incubated at 37° C. for 3 minutes. The latex agglutination reaction was started by mixing the obtained reaction solution with 84 μl of each of the second reagents of Example 1 and Comparative example 1. The absorbance at a wavelength of 800 nm after 1 minute and 2 minutes from the start of the reaction was measured using CS-2000i. The absorbance variation per minute was determined from these measurement results. A specimen (0 μg/ml) not containing D-dimer was also measured in the same manner as described above. The mean value (Mean) of measured value and the standard deviation (SD) on 10 samples of each specimen were calculated. The upper and lower limits of variation of the mean value were calculated by adding a double of the standard deviation to the mean value (+2SD) and subtracting a double of the standard deviation from the mean value (−2SD). These results are shown in Table 4.

TABLE 4

| | Example 1 | | Comparative Example 1 | |
|---|---|---|---|---|
| Sample | 0 μg/mL | 0.25 μg/mL | 0 μg/mL | 0.25 μg/mL |
| 1 | 0.0000 | 0.0007 | 0.0000 | 0.0002 |
| 2 | 0.0002 | 0.0007 | 0.0000 | 0.0002 |
| 3 | 0.0001 | 0.0007 | 0.0000 | 0.0002 |
| 4 | 0.0000 | 0.0010 | 0.0000 | 0.0001 |
| 5 | 0.0000 | 0.0011 | 0.0000 | 0.0005 |
| 6 | 0.0000 | 0.0007 | 0.0000 | 0.0001 |
| 7 | 0.0000 | 0.0008 | 0.0000 | 0.0003 |
| 8 | 0.0001 | 0.0008 | 0.0000 | 0.0003 |
| 9 | 0.0001 | 0.0009 | 0.0000 | 0.0001 |
| 10 | 0.0000 | 0.0008 | 0.0000 | 0.0002 |
| Mean | 0.00005 | 0.00082 | 0.00000 | 0.00022 |
| SD | 0.00007 | 0.00014 | 0.00000 | 0.00012 |
| 2SD | 0.00014 | 0.00028 | 0.00000 | 0.00025 |
| +2SD | 0.00019 | 0.00110 | 0.00000 | 0.00047 |
| −2SD | −0.00009 | 0.00054 | 0.00000 | −0.00003 |

In the reagent of Example 1, it is found that the mean value−2SD on 0.25 μg/ml of the specimen is larger than the mean value+2SD on 0 μg/ml of the specimen. This shows that the upper limit of the variation of the measurement result of 0 μg/ml of the specimen does not overlap with the lower limit of the variation of the measurement result of 0.25 μg/ml of the specimen.

On the other hand, in the reagent of Comparative example 1, it is found that the mean value (−2SD) on 0.25 μg/ml of the specimen is smaller than the mean value (+2SD) on 0 μg/ml of the specimen. This shows that the upper limit of the variation of the measurement result of 0 μg/ml of the specimen may overlap with the lower limit of the variation of the measurement result of 0.25 μg/ml of the specimen.

Therefore, it is suggested that the specimen not containing D-dimer can be distinguished from the specimen containing D-dimer in a low-density region by using the reagent of Example 1, while it is impossible to distinguish between the specimens by using the reagent of Comparative example 1. Therefore, the reagent for assaying D-dimer of the present invention can measure D-dimer in a low-density region with high sensitivity.

What is claimed is:

1. A method of assaying D-dimer in a biological sample comprising:
    mixing the biological sample and a reagent comprising carrier particles comprising a first particle sensitized to a first monoclonal antibody which reacts with D-dimer and a second particle sensitized to a second monoclonal antibody which reacts with D-dimer; and
    measuring a level of aggregation of the particles caused by an antigen-antibody reaction between D-dimer and the first and second monoclonal antibodies in the mixture, wherein
    the first monoclonal antibody reacts with X-fraction, Y-fraction, and D-dimer, but does not react with D- and E-fractions, and
    the second monoclonal antibody reacts with D-dimer, but does not react with X-, Y-, and E-fractions.

2. The method according to claim 1, wherein the second monoclonal antibody does not react with D-fraction.

3. The method according to claim 1, wherein the second monoclonal antibody reacts with D-fraction.

4. The method according to claim 1, wherein the first monoclonal antibody is an antibody produced by a hybridoma deposited with the National Institute of Advanced Industrial Science and Technology under Accession No. FERM BP-11393 on Feb. 17, 2004.

5. The method according to claim 1, wherein the second monoclonal antibody is an antibody produced by a hybridoma deposited with the National Institute of Technology and Evaluation under Accession No. NITE BP-968.

6. The method according to claim 1, wherein the second monoclonal antibody is an antibody produced by a hybridoma deposited with the National Institute of Technology and Evaluation under Accession No. NITE BP-969.

7. The method according to claim 1, wherein, in the measuring step, optically measures the level of aggregation of the particles.

8. The method according to claim 1, wherein, in the measuring step, measures the level of aggregation of the particles by measuring at least one of intensity of scattered light, absorbance, and intensity of transmitted light.

9. The method according to claim 1, wherein, the mixture is a mixture of the biological sample, a reagent comprising a buffer, and the reagent comprising the carrier particles comprising the first particle sensitized to the first monoclonal antibody which reacts with D-dimer and the second particle sensitized to the second monoclonal antibody which reacts with D-dimer.

10. The method according to claim 9, wherein, the mixing step comprises: mixing the biological sample and a reagent comprising a buffer; and mixing a mixture of the biological sample and the reagent comprising the buffer and the reagent comprising the carrier particles comprising the first particle sensitized to the first monoclonal antibody which reacts with D-dimer and the second particle sensitized to the second monoclonal antibody which reacts with D-dimer.

11. The method according to claim 10, wherein the reagent comprising the buffer comprises the first monoclonal antibody and/or the second monoclonal antibody.

12. A method of assaying D-dimer in a biological sample comprising:
    forming a mixture by mixing the biological sample and a reagent comprising carrier particles sensitized to first and second monoclonal antibodies which react with D-dimer, but have different reactivity to D-dimer; and
    measuring a level of aggregation of the particles caused by an antigen-antibody reaction between D-dimer and the first and second monoclonal antibodies in the mixture, wherein
    the first monoclonal antibody reacts with X-fraction, Y-fraction, and D-dimer, but does not react with D- and E-fractions, and
    the second monoclonal antibody reacts with D-dimer, but does not react with X-, Y-, and E-fractions.

13. The method according to claim 12, wherein the second monoclonal antibody does not react with D-fraction.

14. The method according to claim 12, wherein the second monoclonal antibody reacts with D-fraction.

15. The method according to claim 12, wherein the first monoclonal antibody is an antibody produced by a hybridoma deposited with the National Institute of Advanced Industrial Science and Technology under Accession No. FERM BP-11393 on Feb. 17, 2004.

16. The method according to claim 12, wherein the second monoclonal antibody is an antibody produced by a hybridoma deposited with the National Institute of Technology and Evaluation under Accession No. NITE BP-968.

17. The method according to claim 12, wherein the second monoclonal antibody is an antibody produced by a hybridoma deposited with the National Institute of Technology and Evaluation under Accession No. NITE BP-969.

18. The method according to claim 12, wherein, in the measuring step, optically measures the level of aggregation of the particles.

19. The method according to claim 12, wherein, in the measuring step, measures the level of aggregation of the particles by measuring at least one of intensity of scattered light, absorbance, and intensity of transmitted light.

20. A method of assaying D-dimer in a biological sample comprising:
    forming a mixture by mixing the biological sample and a reagent comprising carrier particles comprising a first particle sensitized to a first monoclonal antibody which reacts with D-dimer and a second particle sensitized to a second monoclonal antibody which reacts with D-dimer;
    measuring a level of aggregation of the particles caused by an antigen-antibody reaction between D-dimer and the first and second monoclonal antibodies in the mixture; and
    calculating concentration and/or amount of D-dimer in the biological sample based on the level of aggregation and a calibration curve obtained by measuring a concentration-known D-dimer reference material, wherein
    the first monoclonal antibody reacts with X-fraction, Y-fraction, and D-dimer, but does not react with D- and E-fractions, and
    the second monoclonal antibody reacts with D-dimer, but does not react with X-, Y-, and E-fractions.

* * * * *